United States Patent
Borca et al.

(10) Patent No.: US 8,133,495 B2
(45) Date of Patent: Mar. 13, 2012

(54) LIVE ATTENUATED ANTIGENICALLY MARKED CLASSICAL SWINE FEVER VIRUS

(75) Inventors: Manuel V. Borca, Westbrook, CT (US); Guillermo R. Risatti, Westbrook, CT (US)

(73) Assignees: The United States of America as represented by the Secretary of Agriculture, Washington, DC (US); The University of Connecticut, Farmington, CT (US)

( * ) Notice: Subject to any disclaimer, the term of this patent is extended or adjusted under 35 U.S.C. 154(b) by 180 days.

(21) Appl. No.: 11/805,278

(22) Filed: May 22, 2007

(65) Prior Publication Data
US 2008/0292653 A1    Nov. 27, 2008

(51) Int. Cl.
*A61K 39/155* (2006.01)
*C12P 19/34* (2006.01)
(52) U.S. Cl. .................................. 424/211.1; 435/91.32
(58) Field of Classification Search .................. None
See application file for complete search history.

(56) References Cited

OTHER PUBLICATIONS

Abaza et al. Journal of Protein Chemistry, 1992, vol. 11, No. 5, pp. 433-444.*
Riffkin et al. GENE, 1995, vol. 167, pp. 279-283.*
van Rijn et al. Journal of General Virology, 1996, vol. 77, pp. 2737-2745.*
Heimann et al. Journal of Virology, Feb. 2006, vol. 80, No. 4, pp. 1915-1921.*
Risatti et al. Virology, 2005, vol. 343, pp. 116-127. (Risatti 2005).*
Risatti et al. Virology, 2006, vol. 355, pp. 94-101. (Risatti 2006).*
Risatti et al. Journal of Virology, Mar. 2005, vol. 79, No. 6, pp. 3787-3796. (Risatti Mar. 2006).*
Jungbauer et al. Journal of Biochemical and Biophysical Methods, 2001, vol. 49, pp. 455-465.*

* cited by examiner

*Primary Examiner* — Bao Li
(74) *Attorney, Agent, or Firm* — John D. Pado; Evelyn M. Rabin (57) ABSTRACT

Classical swine fever virus is a world-wide distributed highly-contagious disease affecting swine. The two main strategies for diseases control are prophylactic vaccination and non-vaccination stamping out policies. Marker vaccines are a promising strategy. Here we report the rational development of a doubly antigenic marker CSFV experimental live attenuated candidate strain vaccine (Flag/T4 virus). Flag/T virus (Flag/T4v) is based in the combination of two Brescia derived recombinant attenuated viruses: RB-C22 and T4. RB-C22v contains a 19mer insertion in the structural glycoprotein E1, while T4v posses mutated CSFV amino acid residues 830 to 834 in the structural glycoprotein E2, deleting the highly conserved epitope recognized by monoclonal antibody (mAb) WH303. Flag/T4 virus contains a positive foreign antigenic marker, due to the insertion of the highly antigenic epitope Flag in the 19mer insertion of E1, as well as a negative antigenic marker, the lack of reactivity with mAb WH303. Immunized with Flag/T4v induced a complete protection against the challenge with virulent strain Brescia both at 3 and 28 days post infection when nasally administered and since the second day post infection when intramuscularly administered. These results constitute an example of rational design of a CSFV antigenically marked LAV.

10 Claims, 2 Drawing Sheets

SEQUENCE LISTING

```
<160> NUMBER OF SEQ ID NOS: 7

<210> SEQ ID NO 1
<211> LENGTH: 12357
<212> TYPE: DNA
<213> ORGANISM: Classical Swine Fever Virus
```

```
<400> SEQUENCE: 1
gtatacgagg ttagttcatt ctcgtgtaca tgattggaca aatcaaaatc tcaatttggt      60
tcagggcctc cctccagcga cggccgagct gggctagcca tgcccacagt aggactagca     120
aacggaggga ctagccgtag tggcgagctc cctgggtggt ctaagtcctg agtacaggac     180
agtcgtcagt agttcgacgt gagcagaagc ccacctcgag atgctatgtg gacgagggca     240
tgcccaagac acaccttaac cctagcgggg gtcgttaggg tgaaatcaca ccatgtgatg     300
ggagtacgac ctgataggt gctgcagagg cccactatta ggctagtata aaaatctctg      360
ctgtacatgg cacatggagt tgaatcattt tgaactttta tacaaaacaa acaaacaaaa     420
accaatggga gtggaggaac cggtatacga tgtaacgggg agaccattgt ttggagaccc     480
aagtgaggta cacccacaat caacattgaa gctaccacat gataggggga gaggcaacat     540
caaaacaaca ctgaagaacc tacctaggag aggtgactgc aggagtggca accacctagg     600
cccggttagt gggatatatg taaagcccgg ccctgtcttt tatcaggact acatgggccc     660
agtctatcat agagcccctc tagagttttt tgacgaagca cagttttgtg aggtgaccaa     720
aaggataggt agggtgacag gtagtgacgg aaagctttac catatatacg tgtgcatcga     780
tggttgcatc ctgctgaagc tagccaagag gggcgagcca agaaccctga agtggattag     840
aaatctcacc gactgtccat tgtgggttac cagttgttct gatgatggtg caagtgcaag     900
taaagagaag aaaccagata ggatcaacaa gggtaaatta agatagccc caaaagagca      960 tgagaaggac agcaggacta agccacctga tgctacgatt gtagtggaag gagtaaaata    1020
ccaggtcaaa aagaaaggta agttaaggg aagaataccc caagacggcc tgtaccacaa     1080
caagaataaa ccaccagaat ctaggaagaa attagaaaaa gccctattgg catgggcagt    1140
gatagcaatt atgttatacc aacctgttgc agccgaaaat ataactcaat ggaacctgag    1200
tgacaacggt accaatggta tccagcacgc tatgtacctt agaggagtca gcagaagctt    1260
gcatgggatc tggccagaaa aaatatgcaa aggagtcccc acctacctgg ccacagacac    1320
ggaactgaga gaaatacagg gaatgatgga tgccagcgag gggacaaact atacgtgctg    1380
taagttacag agacatgaat ggaacaaaca tggatggtgt aactggtata acatagaccc    1440
ctggatacag ttgatgaata gaacccaagc aaacttggca gaaggccctc cgagcaagga    1500
gtgcgccgtg acttgcaggt acgataaaaa tgctgacatt aacgtggtca cccaggccag    1560
aaacaggcca accaccctaa ctggctgcaa gaaagggaaa aattttttctt ttgcgggtac    1620 agttatagag ggcccatgta atttcaacgt ttctgttgag gatatcttat atggggatca    1680
tgagtgtggc agtctactcc aggatacggc tctataccta gtagatggaa tgaccaacac    1740
tatagagaga gccaggcagg gagccgcgag ggtgacatct tggctaggga ggcaactcag    1800
aactgccggg aagaggttgg agggcagaag caaaacctgg tttggtgcct atgccctatc    1860
accttattgt aatgtgacaa gcaaaatagg gtacatatgt acactaaca actgtacccc     1920 ggcttgcctc cccaaaaata caaagataat aggccccggt aaatttgaca ctaacgcgga    1980
agacggaaag attctccatg agatgggggg ccacctatca gaatttctgc tgctctctct    2040
ggtcgttctg tctgacttcg cccctgaaac agccagcgcg ttatacctca ttttgcacta    2100
cgtgatccct caatcccatg aagaacctga aggctgtgac acaaaccagc tgaatttaac    2160
agtggaactc aggactgaag acgtgatacc atcatcagtc tggaatgttg caaatatgt    2220 gtgtgttaga ccagactggt ggccatatga aaccaaggtg gctttgttat ttgaagaggc    2280
aggacaggtc gtaaagttag ccttgcgggc actgagggat ttaaccaggg tctggaatag    2340
```

```
cgcatcaacc acggcattcc tcatctgctt gataaaagta ttaagaggac aggtcgtgca   2400
aggtgtgata tggctgttac tggtaactgg ggcacctgtc tcttgtacac atcttgcggc   2460
cgcagattac aaggatgacg acgataaggg ggcacaaggc cggctagcct gcaaggaaga   2520
tcacaggtac gctatatcaa caaccaatga gatagggcta cttggggccg aaggtctcac   2580
taccacctgg aaagaataca accacaattt gcaactggat gatgggaccg tcaaggccat   2640
ctgcatggca ggttccttta aagtcacagc acttaatgtg gttagtagga ggtatctggc   2700
atcattacat aaggacgctt tacccacttc cgtgacattc gagctcctgt tcgacgggac   2760
cagcccattg accgaggaaa tgggagatga cttcgggttc ggactgtgtc cgtatgatac   2820
gagccctgta gtcaagggaa agtacaacac aaccttgttg aatggtagtg cattctacct   2880
agtttgccca ataggtgga cgggtgttat agagtgcacg tcatttaata tggacactct   2940
gagaacagaa gtggtaaaga ccttcagaag agagaaaccc tttccgtaca gaagggattg   3000
tgtgaccact acagtggaaa atgaagatct attctactgt aaatgggggg gcaattggac   3060
atgtgtgaaa ggtgaaccag tgacctacac ggggggggcca gtaaaacaat gcagatggtg   3120
tggcttcgac ttcaatgagc ctgacggact cccacactac cccataggta agtgcatttt   3180
ggcaaatgag acaggttaca gaatagtgga ttcaacggac tgtaacagag atggcgttgt   3240
aatcagcaca gaggggagtc atgagtgctt gattggtaac acaactgtca aggtgcatgc   3300
attagatgaa agactaggcc ctatgccatg caggcctaag gagatcgtct ctagtgcggg   3360
acctgtaagg aaaacttcct gtacattcaa ctacgcaaaa actctgagga acaggtatta   3420
tgagcccagg gacagctatt ccaacaata tatgctcaag ggcgagtatc agtactggtt   3480
tgatctggat gtgaccgacc gccactcaga ttacttcgca gaattcattg tcttggtggt   3540
ggtggcactg ttgggaggaa gatatgtcct gtggctaata gtgacctaca gttctaac    3600 agaacaactc gccgctggtc tacagttagg ccagggtgag gtagtgttaa tagggaactt   3660
aatcacccac acagatattg aggttgtagt atatttctta ctgctctatt tggtcatgag   3720
agatgagcct ataaagaaat ggatactact gctgttccat gctatgacca acaatccagt   3780
taagaccata acagtggcac tgctcatggt tagcgggtt gccaagggtg aaagataga    3840 tggtggttgg cagcggctgc cggagaccaa ctttgatatc caactcgcgc tgacagttat   3900
agtagtcgct gtgatgttgc tggcaaagaa agatccgact accgtcccct tggttataac   3960
ggtggcaacc ctgagaacgg ctaagataac taatggactt agtacagatc tagccatagc   4020
tacagtgtca acagctttgc taacctggac ctacattagt gactattata aatacaagac   4080
cttgctacag taccttatta gcacagtgac aggtatcttc ttgataaggg tactgaaggg   4140
ggtaggtgag ttagatttac acacccaac cttaccatct tacagacccc tcttcttcat   4200
cctcgtgtac ctcatttcca ctgcagtggt aacaagatgg aatctggaca tagccggatt   4260
gctgctgcag tgtgtcccaa ccctttaat ggttttcacg atgtgggcag acatccttac   4320
cctgatcctc atactgccta cttacgagtt gacaaaacta tattacctca aggaagtgaa   4380
gattggggca gaaggggct ggttgtggaa gaccaacttc aagagggtaa atgacatata   4440
cgaagttgac caagctggtg aggggtgta ccttttccca tcaaaacaaa agacaggtac   4500
aataacaggt actatgttgc cattgatcaa agccatactc ataagttgca tcagcaataa   4560
gtggcaattt atatatctat tgtacttgat attcgaagtg tcttactacc ttcacaagaa   4620
gatcatagat gaaatagcag gagggaccaa cttcatctcg agacttgtag ccgctctgat   4680
tgaagccaat tgggccttg acaacgaaga agttagaggt ttaaagaagt tcttcctgct   4740
```

```
gtctagtagg gttaaagaac tgatcatcaa acacaaagtg aggaatgaag tgatggtcca    4800
ctggtttggc gacgaagagg tctatgggat gccgaagctg gttggcttag tcaaggcagc    4860
aacactgagt aaaaataaac attgtatttt gtgcaccgtc tgtgaaaaca gagagtggag    4920
aggagaaacc tgcccaaaat gcggccgttt tgggccacca gtgacctgtg gcatgaccct    4980
agccgacttt gaagaaaaac actataagag gattttcttt agagaggatc aatcagaagg    5040
gccggttagg gaggagtatg cagggtatct gcaatataga gccagagggc aattattcct    5100
gaggaatctc ccggtgctag caacaaaagt caagatgctc ctggtcggaa atcttgggac    5160
ggaggtgggg gatttggaac accttggctg ggtgctcaga gggcctgccg tttgcaagaa    5220
ggttaccgaa catgagaaat gcaccacatc cataatggac aaattaactg ctttcttcgg    5280
tgttatgcca aggggcacca cacctagagc ccctgtgaga ttccccacct ctctcttaaa    5340
gataagaagg gggctggaaa ctggctgggc gtacacacac caaggtggca tcagttcagt    5400
ggaccatgtc acttgtggga aagacttact ggtatgtgac actatgggcc ggacaagggt    5460
tgtttgccaa tcaaataaca agatgacaga cgagtccgag tatggagtta aaactgactc    5520
cggatgcccg gagggagcta ggtgttacgt gttcaaccca gaggcagtta acatatccgg    5580
gactaaagga gccatggtcc acttacaaaa aactggagga gaattcaccct gtgtgacagc    5640 atcagggact ccggccttct tgatctcaa gaacctcaaa ggctggtcag ggctgccgat    5700
atttgaggca tcaagtggaa gagtagtcgg cagggttaag gtcgggaaga atgaggactc    5760
taaaccaacc aagcttatga gtggaataca aacagtctcc aaaagtacca cagacttgac    5820
agaaatggta aagaaaataa caaccatgaa caggggagaa ttcagacaaa taaccccttgc    5880 cacaggtgcc ggaaaaacca cggaactccc tagatcagtc atagaagaga taggaaggca    5940
taagagggtc ttggtcttga tccctctgag ggcggcagca gagtcagtat accaatatat    6000
gagacaaaaa cacccaagca tagcattcaa cttgaggata ggggagatga aggaaggga    6060 catggccaca gggataacct atgcctcata tggttacttc tgtcagatgc acaacctaa    6120 gctgcgagcc gcgatggttg agtactcctt catattcctt gatgagtacc actgtgccac    6180
ccccgaacaa ttggctatca tgggaaagat ccacagattt tcagagaacc tgcgggtagt    6240
agccatgacc gcaacaccag caggcacggt aacaactaca gggcaaaaac accctataga    6300
agaatacata gccccagaag tgatgaaggg ggaagactta ggttcagagt acttggacat    6360
agctggacta aagataccag tagaggagat gaagagtaac atgctggtct ttgtgcccac    6420
aaggaacatg gctgtagaga cggcaaagaa actgaaagct aagggttata actcaggcta    6480
ctattatagt ggagaggatc catctaacct gagggtggta acatcacagt ccccgtacgt    6540
ggtggtagca accaacgcaa tagaatcagg tgttactctc ccagacttgg atgtggtcgt    6600
cgacacaggg cttaagtgtg aaaagaggat acggctgtca cctaagatgc ccttcatagt    6660
gacgggcctg aagagaatgg ctgtcacgat tgggaacaa gcccagagaa gggggagagt    6720
tgggagagtg aagcctggga gatactacag gagtcaagaa accccgttg gttccaaaga    6780 ttaccattac gacctactgc aagcacagag gtacggtata aagatgggga taaacatcac    6840
caaatctttt agagagatga attatgattg gagcctttat gaggaggata gtctgatgat    6900
tacacaattg gaaatcctca caatctgtt gatatcagaa gagctaccaa tggcagtaaa    6960
aaatataatg gccaggactg accacccaga accaatccaa ctggcgtaca acagctacga    7020
aacgcaggtg ccagtgctat tcccaaaaat aaaaatgga gaggtgactg acagttacga    7080
taactatacc ttcctcaacg caagaaagct gggggatgat gtacctccct acgtgtatgc    7140
```

```
cacagaggat gaggacttag cggtagagct gctgggctta gactggccgg accctgggaa   7200
ccaaggaacc gtggaggctg gtagagcact aaaacaagta gttggtctat caacagctga   7260
gaacgccctg ttagtagctt tattcggcta tgtaggatat caggcactct caaagaggca   7320
tataccagta gtcacagaca tatattcaat tgaagatcac aggttggaag acaccacaca   7380
cctacagtat gccccgaatg ctatcaagac ggaggggaag gagacagaat tgaaggagct   7440
agctcagggg gatgtgcaga gatgtatgga agctatgact aattatgcaa gagatggcat   7500
ccaattcatg aagtctcagg cactgaaagt gaaagaaacc cccacttaca aagagacaat   7560
ggacaccgtg gcggactatg taaagaagtt catggaggca ctggcggaca gcaaagaaga   7620
catcataaaa tatgggttgt gggggacgca cacaacctta tataagagca tcggtgctag   7680
gcttgggaac gagactgcgt tcgctaccct ggtcgtgaaa tggctggcat ttgggggaga   7740
atcaatagca gaccatgtca acaagcggc cacagacttg gtcgtttact atatcatcaa   7800
cagacctcag ttcccaggag acacggagac acaacggaga ggaaggaaat ttgtagccag   7860
cctactggtc tcagccctgg ctacttacac ttacaaaagc tggaattaca ataatctgtc   7920
caagatagtt gaaccggctt tggctactct gccctatgcc gccacagctc tcaagctatt   7980
cgcccccact cgattggaga gcgttgtcat actgagtacc gcaatctaca aaacctacct   8040
atcaatcagg cgcggaaaaa gcgatggttt gctaggcaca ggggttagtg cggctatgga   8100
aatcatgtca caaacccag tatctgtggg tatagcggtc atgctagggg tgggggccgt   8160
agcggcccac aatgcaatcg aagccagtga gcagaagaga acactactca tgaaagtttt   8220
tgtaaagaac ttcttggatc aggcagccac tgatgaatta gtcaaggaga gccctgagaa   8280
aataataatg gctttgtttg aagcagtgca gacagtcggc aaccctctta gactggtata   8340 ccaccttttac ggagttttttt acaaaggggtg ggaggcaaaa gagttggccc aaaggacagc   8400
cggtaggaat cttttcactt tgataatgtt tgaggctgtg gaactactgg gagtagatag   8460
cgaaggaaag atccgccagc tatcaagcaa ttacatacta gagctcctgt ataagttccg   8520
tgacagtatc aagtccagcg tgaggcagat ggcaatcagc tgggcccctg ccccttttag   8580
ttgtgattgg acaccgacgg atgacagaat agggcttccc caagataatt tcctccgagt   8640
ggagacaaaa tgcccctgtg gttacaagat gaaagcagtt aagaattgtg ctggggagtt   8700
gagactctta gaagaggaag gctcatttct ctgcaggaat aaattcggga gaggttcacg   8760 gaactcagg gtgacaaaat actatgatga caatctatca gaaataaagc cagtgataag   8820
aatggaagga catgtggaac tctactacaa gggagccact attaaactgg atttcaacaa   8880
cagtaaaaca atattggcaa ccgataaatg ggaggtcgat cactccactc tggtcagggt   8940
gctcaagagg cacacagggg ctggatatcg tgggcatac ctgggtgaga aaccgaacca   9000
caaacatctg atagagaggg actgcgcaac catcaccaaa gataaggttt gttttctcaa   9060
gatgaagaga gggtgtgcat ttacttatga cttatcccct cacaacctta cccggctgat   9120
cgaattggta cacaagaata acttggaaga caaagagatt cctgccgtta cggtcacaac   9180
ctggctggct tacacatttg taaatgaaga tataggggacc ataaaaccag ccttcggga   9240 gaaaataaca ccagagatgc aggaggagat aaccttgcag cctgctgtag tggtggatgc   9300
aactgacgtg accgtgaccg tggtagggga accccctact atgactacag gggagacccc   9360
aacaacgttc accagctcag gtccagaccc gaaaggccaa caagttttaa aactgggagt   9420
aggtgaaggc caatacccg ggactaatcc acagagagca agcctgcacg aagccataca   9480
aagcgcagat gaaaggccct ctgtgttgat attggggtct gataaagcca cctctaatag   9540
```

```
agtgaaaact gtaaagaatg tgaaggtata cagaggcagg gacccactag aagtgagaga    9600
tatgatgagg aggggaaaga tcctagtcat agccctgtct agggttgata atgctctatt    9660
gaaatttgta gattacaaag gcacctttct aactagagag accctggagg cattaagttt    9720
gggtaggcca aaaagaaaa acataaccaa ggcagaagca cagtggttgc tgcgcctcga    9780
agaccaaatg gaagagctac ccgattggtt cgcagccggg gaacccattt ttttagaggc    9840
caatattaaa catgacaggt atcatctggt aggggatata gctactatca aagagaaagc    9900
caaacaattg ggggctacag actctacaaa gatatccaag gaggttggtg caaaagtata    9960
ttctatgaaa ttgagtaatt gggtgatgca agaagaaaac aaacagagca acttgacccc   10020
cttatttgaa gagctcctac agcagtgtcc acccggaggc caaaacaaaa ctgcacatat   10080
ggtctctgct taccaactag ctcaagggaa ctggatgcca accagctgcc atgttttat    10140 ggggaccata tctgccagaa ggactaagac ccatccatat gaagcatatg tcaagttaag   10200
ggagttggta gaggaacaca agatgaaaac attgtgtccc ggatcaagtc tgcgtaagca   10260
caatgaatgg gtaattggca agatcaaata ccagggcaac ctgaggacca aacacatgtt   10320
gaaccccggc aaggtggcag agcaactgca cagagaagga cacagacaca atgtgtataa   10380
caagacaata ggctcagtga tgacagctac tggcatcagg ttggagaagt tgcccgtggt   10440
tagggcccag acagacacaa ccaacttcca ccaagcaata agggataaga tagacaagga   10500
agagaatcta cagaccccgg gtttacataa gaaactaatg gaagttttca atgcattgaa   10560
acgacccgag ttagagtcct cctatgacgc tgtggaatgg gaggaattgg agagaggaat   10620
aaacagaaag ggtgctgctg gtttctttga acgcaaaaac ataggggaga tattggattc   10680
agagaaaaat aaagtagaag agattattga caatctgaaa aagggtagaa atatcaaata   10740
ctatgaaacc gcaatcccaa aaaatgaaaa gagggatgtc aatgatgact ggaccgcagg   10800
tgactttgtg gacgagaaga aacccagagt catacaatac cctgaagcaa aaacaaggct   10860
ggccatcacc aaggtgatgt ataagtgggt gaagcagaag ccagtagtca tacccgggta   10920
tgaagggaag acacctctgt tccaaatttt tgacaaagta aagaaggaat gggatcaatt   10980
ccaaaatcca gtggcagtga gcttcgacac taaggcgtgg gacacccagg tgaccacaaa   11040
tgatctggag ctgataaagg acatacaaaa gtactacttc aagaagaaat ggcataaatt   11100
tattgacacc ctgactatgc atatgtcaga agtacccgta atcactgctg atgggaggt    11160 gtatataagg aaagggcaaa gaggtagtgg acagcccgac acaagcgcag caacagcat    11220 gctaaatgtg ttaacaatgg tttatgcctt ctgcgaggcc acaggggtac cctacaagag   11280
ttttgacagg gtgcaaaaa ttcatgtgtg cggggacgat ggtttcctga tcacagagag   11340
agctctcggc gagaaattcg caagcaaggg agtccaaatc ctgtatgaag ctgggaagcc   11400
ccagaagatc actgaagggg acaaaatgaa agtggcctac caatttgatg atattgagtt   11460
ttgctcccat acaccaatac aagtaaggtg gtcagataac acttctagct acatgccagg   11520
gagaaataca accacaatcc tggctaaaat ggccacaagg ttagattcca gtggtgagag   11580
gggtaccata gcgtacgaga aagcagtagc attcagcttc ctgctaatgt attcctggaa   11640
cccactaatc agaaggattt gcttattggt actatcaact gaactgcaag tgaaaccagg   11700
gaagtcaacc acttactatt atgaagggga cccgatatct gcctacaagg aagtcatcgg   11760
ccacaatctt ttcgatctca agagaacaag cttcgagaag ctggccaagt taaatctcag   11820
catgtccgta ctcggggcct ggactagaca caccagcaaa agactactac aagactgtgt   11880
caatatgggt gttaaagagg gcaactggtt agtcaatgca gacagactgg tgagtagtaa   11940
```

```
gactggaaat aggtatgtac ctggagaagg ccacaccctg caagggagac attatgaaga   12000
actggtgttg gcaagaaaac agatcaacag cttccaaggg acagacaggt acaatctagg   12060
cccaatagtc aacatggtgt taaggaggct gagagtcatg atgatgaccc tgatagggag   12120
aggggtatga gtgcgggtga cccgcgatct ggacccgtca gtaggaccct attgtagata   12180
acactaattt tttatttatt tagatattac tatttattta tttatttatt tattgaatga   12240
gtaagaactg gtacaaacta cctcatgtta ccacactaca ctcattttaa cagcacttta   12300
gctggaagga aaattcctga cgtccacagt tggactaagg taatttccta acggccc     12357
```

<210> SEQ ID NO 2
<211> LENGTH: 9
<212> TYPE: PRT
<213> ORGANISM: Classical Swine Fever Virus

<400> SEQUENCE: 2

Thr Ala Val Ser Pro Thr Thr Leu Arg
1               5

<210> SEQ ID NO 3
<211> LENGTH: 9
<212> TYPE: PRT
<213> ORGANISM: Classical Swine Fever Virus

<400> SEQUENCE: 3

Thr Ser Phe Asn Met Asp Thr Leu Ala
1               5

<210> SEQ ID NO 4
<211> LENGTH: 9
<212> TYPE: PRT
<213> ORGANISM: Classical Swine Fever Virus

<400> SEQUENCE: 4

Thr Ser Phe Asn Met Asp Thr Leu Arg
1               5

<210> SEQ ID NO 5
<211> LENGTH: 8
<212> TYPE: PRT
<213> ORGANISM: Classical Swine Fever Virus

<400> SEQUENCE: 5

Asp Tyr Lys Asp Asp Asp Asp Lys
1               5

<210> SEQ ID NO 6
<211> LENGTH: 46
<212> TYPE: DNA
<213> ORGANISM: Classical Swine Fever Virus

<400> SEQUENCE: 6
ggccgcagat tacaaggatg acgacgataa gggggcacaa ggccgg                 46

<210> SEQ ID NO 7
<211> LENGTH: 46
<212> TYPE: DNA
<213> ORGANISM: Classical Swine Fever Virus

<400> SEQUENCE: 7
ctagccggcc ttgtgccccc ttatcgtcgt catccttgta atctgc                 46

LIVE ATTENUATED ANTIGENICALLY MARKED CLASSICAL SWINE FEVER VIRUS

BACKGROUND OF THE INVENTION

1. Field of the Invention

This invention relates to the design of a double antigenically marked classical swine fever virus (CSFV) live attenuated candidate strain vaccine. The Flag/T4 virus is a recombinant CSFV which contains a positive foreign antigenic marker due to the insertion of the highly antigenic epitope, Flag, into the 19mer insertion of the E1 structural protein of recombinant virus RB-C22, as well as a negative antigenic marker, i.e., changes in the WH303 epitope of the E2 protein which result in the lack of reactivity with monoclonal antibody WH303.

2. Description of the Relevant Art

Classical swine fever (CSF) is a highly contagious disease of swine that can be either acute or chronic in nature (van Oirschot, J. T. 1986. In: *Diseases of Swine*, 6th edition, Leman et al., eds., Iowa State University Press, Ames, Iowa, page 289). The etiological agent, CSF virus (CSFV), is a small, enveloped virus with a positive, single-stranded RNA genome. Along with bovine viral diarrhea virus (BVDV) and border disease virus (BDV), CSFV is classified as a member of the genus *Pestivirus* within the family Flaviridae (Becher et al. 2003. *Virology* 311: 96-104). The 12.5 kb CSFV genome contains a single open reading frame that encodes a 3898 amino acid polyprotein and ultimately yields 11 to 12 final cleavage products (NH2-Npro-C-$E^{rns}$-E1-E2-p7-NS2-NS3-NS4A-NS4B-NS5A-NS5B—COOH) through co- and post-translational processing of the polyprotein by cellular and viral proteases (Rice, C. M. 1996. In: *Fundamental Virology*, 3rd edition, Fields and Howley, eds., Lippincott Raven, Philadelphia, pp. 931-959).

CSFV is enzootic in all continents, and actively circulating in South and Central America, southern Mexico, and the Caribbean. Disease outbreaks occur intermittently in Europe where control programs of the disease (Westergaard et al. 1998. In: *Vaccines in Agriculture: Immunological Applications To Animal Health and Production*, Wood et al., eds., CSIRO, East Melbourne, Australia, pages 13-20) include quarantine and eradication of infected herds, resulting in the elimination of a large number of animals, including noninfected animals, thus engendering significant economic losses. Vaccination, quarantine and testing protocols offer an alternative to these measures and may become the only means to control and eradicate an outbreak of CSF, reducing the economic impact that results from the heretofore elimination of such a vast number of pigs.

Safe and effective CSFV vaccines that prevent clinical symptoms of the disease and virus spreading, including during the early post-vaccination period, have been used around the world (Aynaud, J. M. 1988. In: *Classical Swine Fever and Related Viral Infections*, B. Liess, ed., Nijhoff, Boston, Mass., pages 165-176; Biront and Leunen. 1988. ibid., pages 181-197). Among available CSFV vaccines, live attenuated vaccines, such as C strain, GPE-strain, Thiversal strain, and PAV-250, confer effective and long lasting immunity against CSF (Biront and Leunen, ibid.). In general, these vaccines have been obtained after serial passages of CSFV isolates in tissue culture or rabbits; however, the genetic bases of the attenuation in the above cases are unknown. Additionally, it is not currently possible to distinguish, serologically, between animals vaccinated with live attenuated vaccines and animals infected with wild-type virus.

Development of infectious CSFV cDNA clones has enabled genetic approaches for defining mechanisms of viral replication and pathogenesis. Infectious clones of the attenuated CSFV C-strain and the pathogenic Alfort/Tübingen strain have been constructed, enabling identification of $E^{rns}$ and $N^{pro}$ as virulence factors in swine and the role of different $E^{rns}$ mutations in virus attenuation (Meyers et al. 1996, supra, Moormann et al. 1996. *J. Virol.* 70: 763-770, Ruggli et al. 1996. *J. Virol.* 70:3478-3487, Mayer et al. 2004. *Vaccine* 22: 317-328). CSFV infectious clones have been used to identify viral proteins or protein domains functioning in viral replication and virulence, and to engineer attenuated marker CSF live attenuated vaccines (Meyers et al. 1999, supra, Moser et al. 2001. *Virus Genes* 23: 63-68, Tratschin et al. 1998. *J. Virol.* 72: 7681-7684, van Gennip et al. supra).

The capsid protein, and glycoproteins $E^{rns}$, E1, and E2 are the structural components of the CSFV virion with E1 and E2 anchored to the envelope by their carboxyl termini and $E^{rns}$ loosely associated with the viral envelope (Thiel et al. 1991. *J. Virol.* 65: 4705-4712; Weiland et al. 1990. *J. Virol.* 64: 3563-3569; Weiland et al. 1999. *J. Gen. Virol.* 80: 1157-1165).

E1 and E2 are type I transmembrane proteins with an N-terminal ectodomain and a C-terminal hydrophobic anchor (Thiel et al., supra). E2, the major structural protein, is considered essential for CSFV replication, as virus mutants containing partial or complete deletions of the E2 gene have proven non-viable (van Gennip et al. 2000. *Vaccine* 19:447-459). E2 is the most immunogenic of the CSFV glycoproteins (Konig et al. 1995. *J. Virol.* 69: 6479-6486; van Gennip et al. and Weiland et al. 1990, supra), inducing neutralizing antibodies and protection against lethal CSFV challenge (Wensvoort et al. 1989. *Vet. Microbiol.* 21: 9-20; Van Zijl et al. 1991. *Vaccine* 17: 433-440; Hulst et al. 1993. *J. Virol.* 67: 5435-5442; Rumenapf et al. 1991. *J. Virol.* 65: 589-597; Van Rijn et al. 1996. *J. Gen. Virol.* 77: 2737-2745; Van Rijn et al. 1998. *Vaccine* 17: 433-440). CSFV E2 also contains, between residues 829 and 837, an epitope recognized by monoclonal antibody (mAb) WH303 (Lin et al. 2000. *J. Virol.* 74:11619-11625), a reagent which is routinely used for CSF diagnostics. WH303 mAb does not react with E2 of BVDV or BDV.

Candidate CSFV subunit marker vaccines have been developed using recombinant E2 envelope protein (Van Zijl et al., supra; Hooft van Iddkinge et al. 1996. *Vaccine* 14: 6-12; Hulst et al, 1993, supra; Van Rijn et al., supra). Different E2 protein domains have been described as targets for neutralizing monoclonal antibodies (Wensvoort et al., supra), but E2 subunit vaccines have not been found to be as efficacious as traditional live attenuated vaccines, particularly when animals are challenged shortly after vaccination (Hulst et al., 1993, supra; Van Rijn et al., supra; Risatti et al. 2003. *J. Clin. Microbiol.* 41: 500-505). The failure to induce rapid and efficient protective immunity precludes the use of subunit vaccines as an emergency control measure during a CSFV outbreak. DNA vaccines encoding E2, when expressed, also induced protection in pigs; however, again, rapid elicitation of protection was not proven (Andrew et a. 2000. *Vaccine* 17: 1932-1938; Yu et al. 2001. *Vaccine* 19: 1520-1525).

Recently, infectious clone technology has enabled antigenic modification of attenuated CSFV strains for use as experimental marker live attenuated CSF vaccines. Infectious clones of the attenuated C-strain were used to replace the antigenic region of E2 and/or the complete $E^{rns}$ gene with analogous sequences from Bovine Viral Diarrhea Virus (BVDV). Preliminary data indicated that both chimeric viruses were able to induce protection in pigs at one week after vaccination. Significantly, chimera-induced anti-CSFV antibody responses could be discriminated from those produced by parental virus (van Gennip et al., supra).

The development of disease control strategies in the event of a CSFV outbreak requires rapid onset of protection, which becomes a more important parameter of vaccine performance than, for example, duration of protection. The development of such vaccines would imply the production of rationally designed live attenuated vaccine CSFV strains.

SUMMARY OF THE INVENTION

We have developed a novel classical swine fever mutant virus, the Flag/T4 virus.

In accordance with this discovery, it is an object of the invention to provide a recombinant classical swine fever virus (CSFV) mutant virus, the Flag/T4v virus, comprising DNA encoding a CSFV E1 glycoprotein modified by insertion of the Flag epitope and DNA encoding a CSFV E2 glycoprotein lacking an immunodominant WH303 epitope.

It is also an object of the invention to provide a recombinant classical swine fever virus comprising DNA encoding CSFV E2 glycoprotein which has been modified by progressively mutating a portion of the E2 gene of the highly pathogenic strain Brescia, resulting in the mutated E2 virus more closely resembling the WH303 epitope sequence of the homologous E2 gene from BVDV, a modification resulting in attenuation of CSFV.

An added object of the invention is to provide immunogenic compositions comprising a viable recombinant classical swine fever virus mutant, Flag/T4v.

An additional object of the invention is to provide a rationally designed live attenuated CSFV effective to protect an animal from clinical CSF disease when challenged with virulent Brescia CSFV.

A further object of the invention is to provide a marker vaccine which can potentially distinguish between vaccinated animals and animals infected with CSFV.

A still further object of the invention is to provide a vaccine comprising at least one additional vaccine strain capable of inducing protection against CSF or against another porcine pathogen.

Another object of the invention is to provide a method for protecting an animal against CSF by administering an effective amount of rationally designed live attenuated CSFV vaccine.

Other objects and advantages of this invention will become readily apparent from the ensuing description.

DETAILED DESCRIPTION OF THE INVENTION

Figure 1:
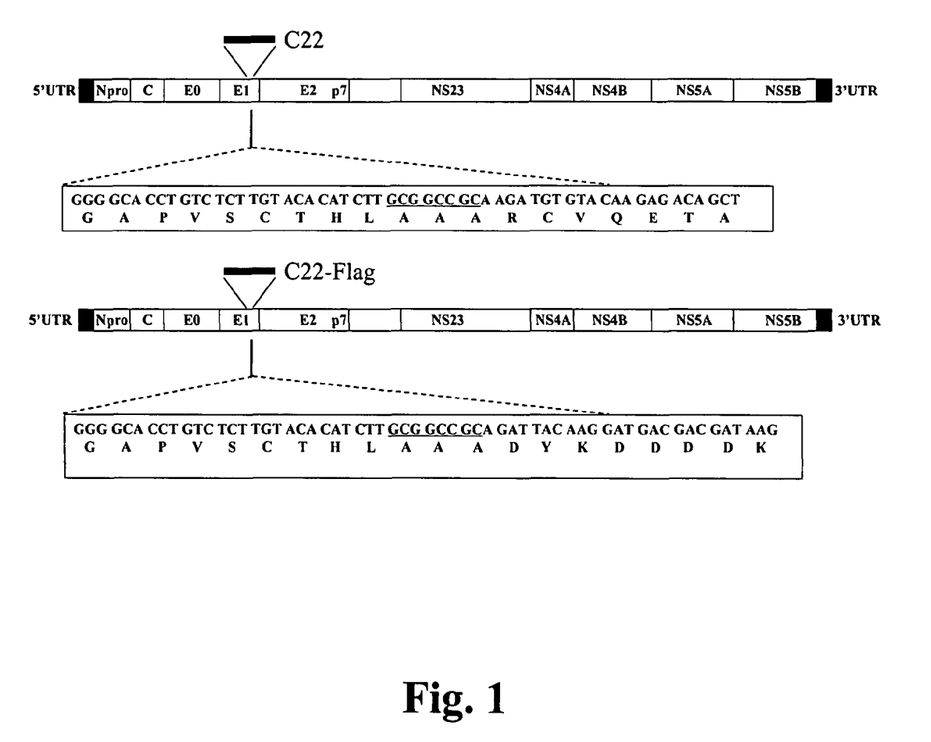
FIG. 1 depicts a schematic representation of the Flag virus. Flag virus is a derivative of CSFV RB-C22 strain (Risatti et. al., 2006. *Virology* 355: 94-101) where a portion of the 19mer insert (GAPVSCTHLAAARCVQETA; SEQ ID NO:8, encoded by SEQ ID NO:10) has been replaced by the FLAG™ epitope (DYKDDDDK; SEQ ID NO:5) resulting in a 20 amino acid insertion (GAPVSCTHLAAADYKD-DDDK; SEQ ID NO:9, encoded by SEQ ID NO:11) in the wild-type E2 glycoprotein sequence. The unique NotI site is indicated in italics.
Figure 2:
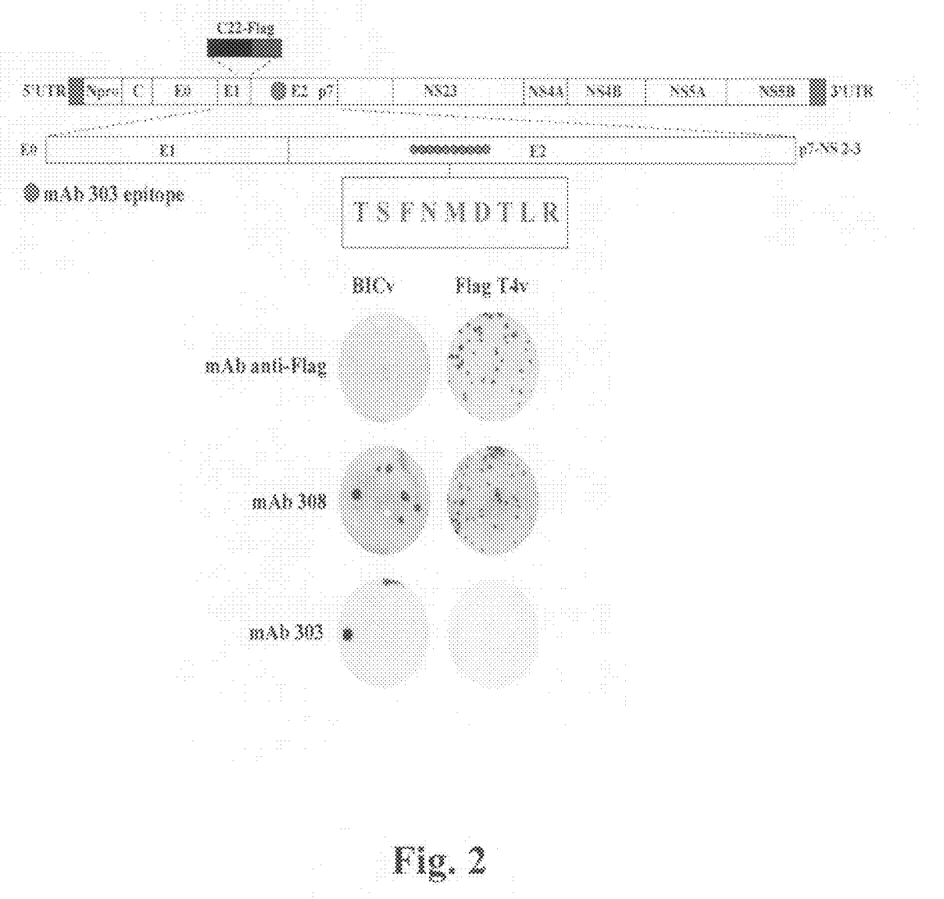
FIG. 2 shows the antigenic phenotype of Flag-T4 and BIC viruses. SK6 monolayers were infected, overlaid with 0.5% agarose and incubated at 37° C. for 3 days. Plates were fixed with 50% (vol/vol) ethanol-acetone and stained by immunohistochemistry with mAbs WH303, anti-Flag or WH308.

We have developed an experimental live attenuated CSFV vaccine strain, Flag/T4 (SEQ ID NO:1), which contains a positive foreign antigenic marker in CSFV structural protein E1 as well as a negative antigenic marker in structural protein E2. Immunization with Flag/T4v induced a complete protection against the challenge with the virulent strain Brescia, both at 3 and 28 days post infection when nasally administered and at the second day post infection when intramuscularly administered. A serological response against the Flag epitope in Flag/T4v-immunized animals allows the discrimination between a Flag/T4v-immunized and a Brescia-infected animal.

The genetic basis and the molecular mechanisms underlying Pestivirus virulence are still unclear. In the case of CSFV, different reports have described associations between viral proteins or specific genomic region with virulence. An in frame insertion of 19 amino acids into E1 gene of CSFV strain Brescia led to attenuation in vivo (Risatti et al. 2005b, supra). A viral mutant, RB-C22v, with a 19 amino acid insertion at nucleotide position 2429, near the carboxyl terminus of E1 glycoprotein, was obtained. Insertion of the 19 amino acid peptide results in complete in vivo attenuation of the virulent CSFV strain Brescia, rendering a virus that resembles CSFV live attenuated vaccines in infected pigs. Unlike the acute fatal disease induced by Brescia and its infectious clone, BICv, RB-C22v infection was subclinical, characterized by decreased viral replication in tonsils, limited generalization of infection, a significant reduction of virus shedding, and significantly lower virus titers in blood, lymph nodes, bone marrow, kidney, spleen, and brain.

Mutations introduced into the WH 303 epitope (epitope which specifically binds to mAb WH303) in E2 glycoprotein of highly pathogenic CSFV strain Brescia also resulted in attenuation of the virus. Progressive changes were introduced into the CSFV Brescia WH 303 epitope (TAVSPTTLR; SEQ ID NO:2) to resemble residues found at the same position (TSFNMDTLA; SEQ ID NO:3) in BVDV strain NADL E2 glycoprotein. The mutant virus T4v (TSFNMDTLR; SEQ ID NO:4) lacks reactivity to mAb WH 303, shows small plaque morphology, i.e., an approximately 70% plaque size reduction compared with parental BICv in SK6 cells, and is significantly attenuated in vivo. Unlike the acute fatal disease induced by BICv, T4v infection is sub-clinical and is characterized by decreased viral replication in target organs and reduced virus shedding. Thus, a novel CSFV genetic virulence determinant associated with E2 glycoprotein has been identified. Although the mechanism underlying the attenuation remains unknown, interestingly, the gradual loss of reactivity with the mAb WH 303 correlated with a loss of virulence in vivo, leading to the final attenuation of CSFV.

The relevance of WH 303 as a major immunodominant epitope has been recently observed during characterization of neutralizing monoclonal antibodies specific for CSFV E2 and Erns using a phage-displayed random peptide library (Zhang et al. 2006. *Archives of Virology* 151 (1): 37-54). Those monoclonal antibodies were found to bind a common motif SPTxL (SEQ ID NO:12) that also map to WH 303 epitope (SPTTL; SEQ ID NO:13). Furthermore, multi peptide-vaccines, containing the WH 303 epitope, consisting of six overlapping peptides ranging between 20 to 25 amino acids length induced immunity against CSFV (Dong et at. 2005. *Vaccine* 23:3630-3633).

Construction of the live attenuated vaccine of the invention, a Flag/T4v mutant, is based on two previously described viral mutants: the RB-C22v mutant, which has a 19 amino acid insertion at nucleotide position 2429, near the carboxyl terminus of the E1 glycoprotein (Risatti et al. 2006, supra) and the mutant T4v, a mutant virus having a mutation in the CSFV E2 glycoprotein, i.e., in the highly specific and conserved CSFV WH303 epitope of E2 (Risatti et al. 2005. *Virology* 343: 116-127). The Flag/T4v mutant virus vaccine was constructed by inserting the oligonucleotide encoding the highly antigenic epitope Flag, DYKDDDDK(SEQ ID NO:5), into the 19 mer insertion of the CSFV E1 polypeptide and introducing a mutation into the region covered by amino acid positions 829-834 of the WH303 epitope of E2, changing TAVSPTTLR to TSFNMDTLR. Thus, the resulting Flag/T4v mutant virus vaccine has dual advantages. Those animals vaccinated with Flag/T4v exhibit a positive specific response to the Flag epitope and at the same time, are expected to lack reactivity with viral epitopes recognized by a monoclonal antibody which specifically recognizes WH303. Thus, this viral mutant has the potential of being utilized as an attenuated marker vaccine, useful for the discrimination between Flag/T4v-immunized and Brescia-infected animals.

A vaccine is defined herein as a biological agent which is capable of providing a protective response in an animal to which the vaccine has been delivered and is incapable of causing severe disease. Administration of the vaccine results in immunity from a disease; the vaccine stimulates antibody production or cellular immunity against the pathogen causing the disease. Immunity is defined herein as the induction of a significant higher level of protection in a population of swine against mortality and clinical symptoms after vaccination compared to an unvaccinated group. In particular, the vaccine according to the invention protects a large proportion of vaccinated animals against the occurrence of clinical symptoms of the disease and mortality. The vaccine of the invention herein is a genetically engineered mutant virus vaccine. A marker vaccine is defined as a vaccine that, in conjunction with a diagnostic test, enables serological differentiation of vaccinated animals from infected animals. A mutation is understood to be a change in the genetic information of a "wild-type" or unmodified E1 or E2 gene of a parent CSFV strain which is able to express native E1 and E2 proteins. Thus, the E1 and E2 polypeptides expressed by the Flag/T4v mutant virus are changed: the E1 protein displays a Flag epitope within the altered (by insertion) E1 protein and the E2 protein lacks a wild-type immunodominant WH303 epitope.

A Flag/T4v mutant according to the present invention was generated by introducing a mutation in the gene encoding the WH303 epitope such that the ability of the immunodominant CSFV epitope to react with mAb WH303, the mAb specific for the WH303 epitope was lost. Example 5 demonstrates that the Flag/T4v (FTv) mutant according to the invention is able to protect FTv-infected animals challenged with BICv. No challenge virus was detected in nasal, tonsil, or blood samples. Detection was performed using mAb WH303, the mAb specific for the challenge virus BICv.

A further requirement of the mutation introduced in the E1 and E2 genes is that the altered E1 and E2 genes allow the recovery of infectious Flag/T4v virus from cell culture after transfection of these cells with the appropriate plasmids. Example 3 describes an experiment that is suitable for determining the ability of the infectious Flag/T4v to respond to WH303-specific and FLAG-specific antibodies and the permissibility of the mutation to generate infectious virus recoverable from cell culture transfected with the appropriate plasmids.

A vaccine against CSFV is provided that comprises a Flag/T4v mutant as defined above in a live form, and a pharmaceutically acceptable carrier or diluent. The vaccine according to the invention containing the live virus can be prepared and marketed in the form of a suspension or in a lyophilized form and additionally contains a pharmaceutically acceptable carrier or diluent customary used for such compositions. Carriers include stabilizers, preservatives and buffers. Suitable stabilizers are, for example SPGA (sucrose, phosphate, glutamate, and human albumin), carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are well known in the art. Furthermore, nucleic acid sequences encoding polypeptides for pharmaceutical or diagnostic applications, in particular immunomodulators such as lymphokines, interferons or cytokines, may be incorporated into the vaccine.

A vaccine according to the invention can be prepared by conventional methods such as those commonly used for the commercially available live attenuated CSFV vaccines. Briefly, a susceptible substrate is inoculated with the Flag/T4v mutant and propagated until the virus has replicated to a desired titer after which Flag/T4v-containing material is harvested. Subsequently, the harvested material is formulated into a pharmaceutical preparation with immunizing properties.

Every substrate which is able to support the replication of Flag/T4v viruses can be used in the present invention, including Swine kidney cells (SK6) and primary cultures of swine peripheral blood macrophages.

The vaccine may be administered by intramuscular, intradermal, subcutaneous or intranasal inoculation or injection in an amount which is effective to protect the animal against challenge by a virulent strain of CSFV. This amount may vary according to the animal being inoculated, taking into consideration the size and weight of the animal. The vaccine according to the invention comprises an effective dosage of the Flag/T4v mutant as the active component, i.e. an amount of immunizing Flag/T4v material that will induce immunity in the vaccinated animals, swine, against challenge by a virulent CSFV. Immunity is defined herein as the induction of a significant higher level of protection in a population of swine against mortality and clinical symptoms after vaccination compared to an unvaccinated group. In particular, the vaccine according to the invention prevents a large proportion of vaccinated animals against the occurrence of clinical symptoms of the disease and mortality. Typically, the live vaccine can be administered in a dose of $10^4$-$10^5$ $TCID_{50}$. Effective amounts may be experimentally determined as necessary by those of skill in the art by following the guidance provided by specific Example 5.

In addition to the Flag/T4v mutant, the invention can also include combination vaccines comprising a vaccine strain capable of inducing protection against another porcine pathogen.

The Flag/T4v marker vaccine described above, in conjunction with a diagnostic method, has the potential of distinguishing between animals that are vaccinated with it and animals that are infected with naturally occurring CSFV strains or vaccinated with conventional CSFV vaccines.

The present invention also provides an invaluable tool to monitor CSFV control measures that may lead to eradication of CSFV if applied in large scale stamping out programs. This tool concerns a method for determining CSFV infection in swine comprising the step of examining a sample of the animal for the presence or absence of antibodies reactive with the immunodominant epitopes FLAG and WH303. The sample of the animal used in this method may be any sample in which CSFV or Flag/T4v antibodies can be detected, e.g. a blood, serum or tissue sample.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent, chemiluminescent, radioactive or dye molecules.

Suitable methods for the detection of WH303 and FLAG in the sample include, for example, the enzyme-linked immunosorbent assay (ELISA), immunofluorescent tests and Western blot analysis.

Porcine anti-CSFV sera raised against the Flag/T4v mutant according to the present invention has the potential of being distinguishable from porcine sera raised against naturally occurring CSFV strains and conventional CSFV vaccine strains. Thus, the Flag/T4v mutant has the potential of being a marker vaccine.

Thus, the particular CSFV mutant, Flag/T4v, according to the present invention has the potential of producing antiserum in pigs wherein the antisera are lacking in antibodies that react with an immunodominant epitope, WH303. Such antiserum would score negative in a direct- or blocking WH303 enzyme-linked immunosorbant assay (ELISA).

In an ELISA to detect porcine anti-FLAG and anti-WH303 epitope porcine antibodies, microtitration plates are coated with FLAG-bearing E1 protein (or a FLAG antigen) or wild type E2 protein bearing the WH303 epitope (or an E2 fragment bearing the WH303 epitope). Next, the wells of the coated plates are filled with porcine serum and serial dilutions are made. After incubation, porcine anti-FLAG or anti-WH303 epitope protein serum antibodies are determined by detecting antibody (monoclonal or polyclonal) with the same specificity as the coated one, but which is labeled (e.g. with biotin). The labeled antibody will occupy the free antigens that have not been occupied by anti-WH303 epitope or anti-FLAG antibodies in the porcine serum. For example, horse radish peroxidase coupled to avidin may be added and the amount of peroxidase is measured by an enzymatic reaction. If no antibodies against FLAG-marked E1 or the E2 WH303 epitope are present in the porcine serum sample then a maximum absorption is obtained. If the serum contains many antibodies against the WH303 epitope then a low absorption is expected. Alternatively, after the incubation with porcine serum, the amount of antibodies present in the serum that bound to the WH303 epitope antigen may be determined directly by using an anti-porcine conjugate followed by the enzymatic reaction.

In a sandwich ELISA the wells of a polystyrene microtitration plate can be coated with a monoclonal antibody directed against the WH303 epitope protein, i.e., mAb WH303. Next, the wells of these coated plates are incubated with antigen. After the antigen is captured, the wells are filled with the porcine serum and serial dilutions are made. Subsequently, the protocol as described above may be followed.

In another diagnostic test (Western blot analysis), the FLAG-marked E1 polypeptide or FLAG fragment or the WH303 epitope-containing material is subjected to SDS-PAGE. Next, the separated proteins are electroblotted onto nitro-cellulose membrane. Thereafter, the membranes can be cut into lanes and the lanes are incubated with the porcine serum. The presence in the sample of antibodies specific for the WH303 epitope or antibodies specific for FLAG can be determined by examining whether antibodies bound to the WH303 epitope or the FLAG antigen, for example by using an anti-porcine conjugate followed by an enzymatic reaction. If antibodies against the WH303 epitope or FLAG are present then a band of the appropriate size is identifiable.

The WH303 epitope-containing polypeptide may be any WH303 epitope-containing protein or fragment comprising material which allows the formation of the WH303 epitope antigen-WH303 mAb complex. Similarly, the FLAG-containing polypeptide may be any FLAG-containing protein or fragment comprising material which allows the formation of the FLAG (antigen)-anti-FLAG (antibody) complex. Preferably, the WH303 epitope antigen and the FLAG antigen comprise the expression product of a conventional recombinant host cell or virus, e.g. such as E. coli expressed or baculovirus expressed protein. In a further embodiment of the present invention, a diagnostic test kit is provided which is suitable for performing the diagnostic test according to the invention as described above.

In particular, a diagnostic test kit is provided which comprises in addition to the components usually present, the WH303 epitope antigen or FLAG antigen (if desired, coated onto a solid phase) as the immunological reagent. Other components usually present in such a test kit include, biotin or horseradish peroxidase conjugated antibodies, enzyme substrate, washing buffer etc.

To determine CSFV (BICv) WH303 antigen or FLAG antigen in a test sample from an animal in the field, WH303 mAb and anti-FLAG mAb are used as the immunological reagent, preferably fixed to a solid phase. The test sample is added, and after an incubation time allowing formation of the antibody-antigen complex, a second labeled antibody may be added to detect the complex.

Typically, the absorbance (OD) cut-off value for the ELISA to differentiate positive from negative samples is set at three standard deviations above the average P/N ratios of negative control samples from pigs (where P=the OD of samples from wells coated with a relevant peptide coupled to a carrier molecule and; N=the OD of samples from wells coated with the carrier molecule). A carrier molecule can be a carrier protein, such as BSA, ovalbumin, KLH, a carbohydrate chain or a synthetic amino acid chain.

In an alternative embodiment of the diagnostic method the presence of specific antibodies in porcine serum is examined by incubating the serum and an appropriate antigen in the presence of a monoclonal antibody that specifically reacts with an epitope located within the E2 region.

The recombinant FLAG/T4v mutant according to the invention is obtained after transfection of suitable cells (e.g., SK6 cells) with the synthetic RNA transcript of the FLAG/T4v mutant genome by electroporation. Finally the recombinant FLAG/T4v mutant is harvested from the supernatant of the transformed cells.

It has also been found that FLAG/T4v mutant according to the present invention is able to induce a protective immune response, i.e. animals immunized with a vaccine comprising the FLAG/T4v mutant are protected against virulent challenge. Moreover, it has been found that antisera of animals infected with naturally occurring CSFV comprise antibodies directed to the WH303 epitope of BICv. Antisera from animals infected with the FLAG/T4v mutant virus according to the present invention can be tested according to the methods described above to determine their reactivity with the Flag and WH303 epitope. In addition, it has been found that the FLAG/T4v mutant virus as described above is attenuated if compared with the parent BICv virus which is able to produce the native E1 and E2 proteins.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al. 1990. *Dtsch. Tierarztl. Wochenschr.* 97: 77-79), free of BVDV, were cultured in Dulbecco' minimal essential medium (DMEM) (Gibco, Grand Island, N.Y.) with 10% fetal calf serum (FCS) (Atlas Biologicals, Fort Collins, Colo.). CSFV Brescia strain was propagated in SK6 cells and used for the construction of an infectious cDNA clone (Risatti et al. 2005. *J. Virol*. 79: 3787-3796). Titration of CSFV from clinical samples was performed using SK6 cells in 96 well plates (Costar, Cambridge, Mass.). Viral infectivity was detected, after 4 days in culture, by immunoperoxidase assay using the CSFV monoclonal antibodies 174 (kindly provided by Georgina Ibata, Veterinary Laboratory Agency, UK) and the Vectastain ABC kit (Vector Laboratories, Buringames, Calif.). Titers were calculated using the method of Reed and Muench (1938. *Amer. J. Hygiene* 27: 493-497) and expressed as $TCID_{50}$/ml. As performed, test sensitivity was >1.8 $TCID_{50}$/ml. Plaque assays were performed using SK6 cells in 6 well plates (Costar). SK6 monolayers were infected, overlaid with 0.5% agarose and incubated at 37° C. for 3 days. Plates were fixed with 50% (vol/vol) ethanol-acetone and stained by immunohistochemistry with mAbs 174, WH303, WH308 (Edwards et al. 1991. *Vet Microbiol*. 29:101-108) or anti-Flag (Sigma).

Example 2

Construction of CSFV Flag-T4 Virus

A full-length CDNA copy of RB-C22v (Risatti et al. 2006., supra) was NotI-NheI digested and the excised 46 nucleotide fragment replaced with an oligonucleotide, forward sequence 5'GGCCGCAGATTACAAGGATGACGACGATAAGGGGGCACAAGGCCGG 3' (SEQ ID NO:6) and reverse complementary sequence 5'CTAGCCGGCCTTGTGCCCCCTTATCGTCGTCATCCTTGTAATCTGC 3' (SEQ ID NO:7), encoding for the flag epitope DYKDDDDK (bold case). One hundred pmoles of the forward and reverse oligonucleotides were annealed in buffer containing 10 mM Tris, pH 7.5-8.0, 50 mM NaCl, 1 mM EDTA. Oligos were heated at 95° C. for 5 min and cooled at room temperature for 30 min. Annealed oligonucleotides were directionally cloned into NotI-NheI-digested pRB-C22 using T4 DNA ligase (New England Biolabs, Beverley, Mass.). The introduction of mutations in amino acids at positions 829-834 of the CSFV polyprotein resulting in a shift of the Brescia amino acid sequence (TAVSPT) to the corresponding residues in bovine viral diarrhea virus (BVDV) strain NADL (TSFNMD) were performed on the pFlag-T4 exactly as described by Risatti et al. (2005. *Virology* 343: 116-127) for the development of the T4 virus.

Infectious RNA was in vitro transcribed from full-length infectious clones of the Flag-T4 virus (FTv) (FIGS. 1 and 2) and used to transfect SK6 cells. Viruses were rescued from transfected cells by day 4 post-transfection. Nucleotide sequences of the rescued virus genomes were identical to parental DNA plasmids, confirming that only mutations at predicted glycosylation sites were reflected in rescued viruses.

Example 3

In Vitro Rescue of CSFV Brescia and Glycosylation Mutants

Full-length genomic infectious clones were linearized with SrfI and in vitro transcribed using the T7 Megascript system (Ambion, Austin, Tex.). RNA products were precipitated with LiCl and transfected into SK6 cells by electroporation at 500 volts, 720 ohms, 100 watts with a BTX 630 electroporator (BTX, San Diego, Calif.). Cells were plated in 12 well plates and incubated for 4 days at 37° C. and 5% $CO_2$ atmosphere. Virus was detected by immunoperoxidase staining as described above and stocks of rescued viruses were stored at −70° C.

In vitro growth characteristics of FTv were evaluated relative to parental BICv in a single step growth curve. SK6 cell cultures were infected at a MOI of one $TCID_{50}$ per cell. Virus was adsorbed for 1 h (time zero), and samples were collected at 48 h post-infection (PI). Results demonstrated that FTv exhibited growth characteristics practically indistinguishable from BICv reaching titers of 6.10 (SD: 0.45) $TCID_{50/ml}$ versus 6.04 (SD:07) of BICv.

Additionally, FTv was tested for their plaque size in SK6 cells, exhibiting a noticeable reduction in plaque size relative to BICv (FIG. 2). This small plaque phenotype is expected since both parental viruses, RB-C22 and T4v, possess small plaque compared with their parental virus BIC (Risatti et al. 2005, 2006, supra).

Reactivity of Flag-T4 virus against mAbs anti-Flag, WH303 and WH308 was performed in order to analyze its antigenic phenotype. Flag-T4 virus strongly reacts with mAbs anti-Flag and WH308 and completely fails to react with mAb WH303. The WH308 epitope is located between residues 882 and 1064 of the CSFV E2 polypeptide, a region of E2 different from the epitope identified by WH303 (Risafti et al. *Virology* (in press). Conversely, BICv reacts with mAbs WH303 and WH308 and fails to react with mAb anti-Flag (FIG. 2).

Example 4

DNA Sequencing and Analysis

Full-length infectious clones and in vitro rescued viruses were completely sequenced with CSFV specific primers by the dideoxynucleotide chain-termination method (Sanger et al. 1977. *Proc. Natl. Acad. Sci*. USA 74: 5463-5467). Viruses recovered from infected animals were sequenced in the mutated area. Sequencing reactions were prepared with the Dye Terminator Cycle Sequencing Kit (Applied Biosystems, Foster City, CA). Reaction products were sequenced on a PRISM 3730xl automated DNA Sequencer (Applied Biosystems). Sequence data were assembled with the Phrap software program (www.phrap.org), with confirmatory assemblies performed using CAP3 (Huang and Madan. 1999. *Genome Res*. 9: 868-877). The final DNA consensus sequence represented, on average, five-fold redundancy at each base position. Sequence comparisons were conducted using BioEdit software (Retrieved from the Internet: <URL: mbio.ncsu.edu/BioEdit/bioedit.html)

Example 5

Animal Infections

The ability of Flag-T4 virus to induce protection against virulent BICv was assessed in early and late vaccinationexposure experiments. For protection studies, 12 pigs were randomly allocated into 3 groups of 4 animals each. Pigs in Groups 1 and 2 were inoculated intranasally with $10^5$ $TCID_{50}$ Flag-T4, and pigs in Group 3 were mock infected. At 3 DPI (Group 1) or 28 DPI (Group 2), animals were challenged with $10^5$ $TCID_{50}$ BICv along with animals in Group 3. Clinical signs and body temperature were recorded daily-throughout the experiment as described above. Blood, serum, nasal swabs and tonsil scrapings were collected at times post-challenge, with blood obtained from the anterior vena cava in EDTA containing tubes (Vacutainer) for total and differential white blood cell counts. Total and differential white blood cell and platelet counts were obtained using a Beckman Coulter ACT (Beckman, Coulter, Calif.).

Mock-vaccinated control pigs receiving BICv only (Group 3) developed anorexia, depression, and fever by 4 days post-challenge (Table 1), and a marked reduction of circulating leukocytes and platelets by 4 DPC (data not shown), and died or were euthanized in extremis by 9-10 DPC. Notably, FTv induced complete protection by 3 DPI. All pigs survived infection and remained clinically normal, without significant changes in their hematological profiles after challenge (data not shown).

TABLE 1

Survival and fever response following challenge with BICv post FT4v infection.

| Challenge Group | No. of Survivors/ Total No. | Mean time to Death (Days ± SD) | Fever: Days to Onset (Days ± SD) | Fever: Duration (Days ± SD) |
|---|---|---|---|---|
| 3 DPI | 4/4 | — | — | — |
| 28 DPI | 4/4 | — | — | — |
| Mock Vaccinated | 0/4 | 12 (0) | 4.5 (0.7) | 9.5 (0.7) |

Viremia and virus shedding of vaccinated-exposed animals were examined at 3, 4, 5, 8, 12, 14, and 21 DPC (Table 2). Detection was performed using mAb WH303, the mAb specific for the challenge virus BICv. As expected, in mock-vaccinated control animals, viremia was observed by 4DPC, with virus titers remaining high by 8 DPC ($10^{7.05}$ $TCID_{50}$/ml, SD: 0.11). Furthermore, virus was detected in nasal swabs and tonsil scrapings of mock-vaccinated animals after 4 DPC. Conversely, in FTv-infected animals, challenged either at 3 or 28 DPI, no challenge virus was detected in nasal, tonsil, or blood samples during the 21 day observation period (Table 2). These results indicated that protection induced by FTv was solid, preventing both the presentation of CSF related clinical signs and the replication of the challenge virus.

TABLE 2

Detection of virus[a] in nasal swabs, tonsil scrapings, and blood samples after challenge of N1v-vaccinated animals with virulent BICv.

| Challenge Group[e] | Sample | 3 | 4 | 6 | 8 | 12 | 14 | 21 |
|---|---|---|---|---|---|---|---|---|
| | | Days Post-Challenge | | | | | | |
| 3 DPI | Nasal | nd[b] | nd | nd | nd | nd | nd | nd |
| | Tonsil | nd | nd | nd | nd | nd | nd | nd |
| | Blood | nd | nd | nd | nd | nd | nd | nd |
| 28 DPI | Nasal | nd | nd | nd | nd | nd | nd | nd |
| | Tonsil | nd | nd | nd | nd | nd | nd | nd |
| | Blood | nd | nd | nd | nd | nd | nd | nd |

TABLE 2-continued

Detection of virus[a] in nasal swabs, tonsil scrapings, and blood samples after challenge of N1v-vaccinated animals with virulent BICv.

| Challenge Group[e] | Sample | 3 | 4 | 6 | 8 | 12 | 14 | 21 |
|---|---|---|---|---|---|---|---|---|
| | | Days Post-Challenge | | | | | | |
| Mock Vaccinated | Nasal | nd | 1.9 (0)[c] | 3.5 (0) | 4.3 (1) | D[d] | D | D |
| | Tonsil | nd | 2.8 (0.4) | 2.9 (0.7) | 4.5 (0.1) | D | D | D |
| | Blood | nd | 3.9 (0.4) | 6.7 (0.6) | 7.0 (0.1) | D | D | D |

[a]Virus detection was performed using mAb WH303.
[b]n.d. (not detectable): virus titers equal or less than 1.8 $TCID_{50}$ (log 10).
[c]number in parentheses indicate Standard Deviation for 4 animals.
[d]D: Dead animals.
[e]n = 4 animals/group CSFV, when intranasally inoculated, replicate primarily in tonsils, and from there the infection expands to secondary target lymph organs. Therefore, virus replication in tonsils is a critical step in the animal infection after the intranasal inoculation of CSFV. In order to gain insight into the kinetics of viral replication at early times after infection, the presence of FTv and BICv in the main target organs was analyzed at different times after FTv infection or after the challenge with BICv. A group of animals (n=6) were intranasally infected with $10^5$ $TCID_{50}$ of either Flag-T4 or BIC viruses, or with FTv and 3 days later challenged with BICv. Two animals per group were euthanized at 3, 5, and 7 DPI in groups infected with FTv or BICv and at 1, 3, 5, and 7 days post-challenge in animals infected with FTv and challenged with BICv. Tonsils, mandibular, MLN, RPLN, and spleen were immediately removed after necropsy. The presence of each virus in all collected organs was examined by virus titration on SK6 cells. As expected, the highest titers are shown in tonsils at 3 OPI with increasing levels at 5 and 7 DPI (Table 3). In contrast, animals infected with FTv presented virus titers (detected by mAb anti-Flag) in tonsils at 3 DPI with a slight increase by day 5 and 7 PI, although titers were 100 to 10000 times lower when compared with tonsils in BICv-infected animals (Table 3). RPLN and MNL in FTv-infected animals showed virus titers only at 3 and 5 DPI with levels 10-100 fold lower than in BICv-infected animals (Table 3). These results indicate that replication of FTV in intranasally infected animals remains restricted to the tonsils and its draining lymph nodes. Remarkably, in FTv-infected/BICv-challenged animals, all organs presented negative BICv titers at all time points tested (1, 3, 5, and 7 DPC) (Table 3). These results support the observation that after challenge, BICv does not replicate in FTv-infected animals.

TABLE 3

Titers of virus in organs of animals infected with Flag-T4 virus, BICv or infected with Flag-T4 virus and challenge with BICv.

| Virus | DPI or DPC | Tonsil | RFLN | MLN | Spleen |
|---|---|---|---|---|---|
| | | Log 10 $TCID_{50}$/g in: | | | |
| Flag-T4[e] | 3[a] | 2.1 (0.2)[g] | nd[d] | 1.9 (0) | nd |
| | 5 | 4.8 (0) | 2.6 (0.6) | 2.1 (0.2) | nd |
| | 7 | 4.1 (1.6) | nd | nd | nd |
| BIC[f] | 3[a] | 4.4 (1) | 2.6 (0.4) | 2.88 (0.3) | 2.1 (0.1) |
| | 5 | 6.3 (0) | 4.3 (0) | 4.6 (0.7) | 4.5 (0) |
| | 7 | 6.9 (0.8) | 6.3 (0.2) | 6.9 (1.1) | 6.2 (1) |
| Flag-T4/ BICv[c,f] | 1[b] | nd | nd | nd | nd |
| | 3 | nd | nd | nd | nd |

TABLE 3-continued

Titers of virus in organs of animals infected with Flag-T4 virus,
BICv or infected with Flag-T4 virus and challenge with BICv.

| Virus | DPI or DPC | Log 10 TCID$_{50}$/g in: | | | |
|---|---|---|---|---|---|
| | | Tonsil | RFLN | MLN | Spleen |
| | 5 | nd | nd | nd | nd |
| | 7 | nd | nd | nd | nd |

[a] DPI: days post-infection.
[b] DPC: days post-challenge with BICv.
[c] Animals were infected with Flag-T4 and 3 days later challenged with BICv.
[d] not detectable: virus titers equal or less than 1.8 TCID$_{50}$ (log 10).
[e] Virus titers detected with mAb anti-Flag.
[f] Virus titers detected with mAb WH303.
[g] Number in Parentheses indicate Standard Deviation for 2 animals.

Intramuscular (IM) administration of Flag-T4 virus induces protection at second day post infection. The early induction of protection after vaccination is of paramount importance during a disease outbreak. Therefore, the ability of FTv to induce protection earlier then 3 DPI was assessed. Four groups of animals (n=2) were IM infected with $10^5$ TCID$_{50}$ of FTv and challenged intranasally with $10^5$ TCID$_{50}$ of BICv at 24, 48, or 72 h later. Interestingly, animals challenged at 24 and 48 h post FTv infection remained clinically normal during the 21 day experimental period. One of the animals challenged at 24 h after FTv virus infection presented CSFV clinical signs being euthanized at 15 DPC while the other remained clinically normal.

Thus, an experimental live attenuated vaccine strain has been rationally developed. The strain contains positive and negative antigenic markers which confer solid protection at 3 DPI, when delivered intranasally and at 2 DPI when administered by the intramuscular route.

Example 6

Immunofluorescence and Confocal Microscopy

To confirm the results cited above in Example 5, the presence of FTv and BICv in tonsil tissues were evaluated by immunofluorescence using mAbs anti-Flag or WH303. Triplicate samples were collected postmortem of selected tissues (palatine tonsil, mandibular lymph node (MLN), retropharyngeal LN (RPLN), and spleen). The tissues were mounted n blocks using Optimal cutting temperature ( ) OCT) compound (TissueTek), promptly frozen in liquid nitrogen and stored at −70° C. Four µm thick sections of cryopreserved tissues from all three samples of all animals were sectioned with a cryomicrotome and fixed with acetone for 10 min at −20° C. After fixation, the sections were incubated in blocking buffer (PBS, 2% bovine serum albumin, 20% normal bovine serum) for 1.5 hours at room temperature (RT). Primary mAbs (mAb anti-Flag M2 and WH303) were diluted in blocking buffer and incubated with the sections overnight at 4° C. in a humid chamber. After washing five times with PBS, the sections were incubated with the appropriate secondary antibody, goat anti-mouse isotype-specific IgG (AlexaFluor 488 or AlexaFluor 594, Molecular Probes) diluted in blocking buffer, for 1.5 hours at 37° C. following this incubation, the sections were washed 5 times with PBS, counterstained with TOPRO-iodide 642/661 (Molecular Probes) for 5 min at RT, washed as before, mounted, and examined in a Leica scanning confocal microscope. Data were collected utilizing an appropriate control lacking the primary antibodies in order to determine channel crossover settings, as well as using these antibodies in uninfected tissues to give the negative background level and to determine channel cross-over settings. The captured images were adjusted-for contrast and brightness using Adobe Photoshop software.

Results completely corroborate the results obtained by virus titration (Table 4). Tonsils from animals infected with FTv showed a weak but clear fluorescence signal with mAb anti-Flag on days 3, 5, and 7 PI. Moreover, tonsils of BICv-infected animals showed strong reactivity with mAb WH303 at all days tested. Although mAb anti-Flag reactivities, comparable to that of FTv-infected animals, were detected in tonsils of FTv-infected/BICv challenged animals, no signal with mAb WH303 was detected in tonsils at any of the times tested (1, 3, 5, and 7 DPC).

TABLE 4

Detection by immunofluorescence of Flag-T4 and BIC viruses
in swine tonsils from animals[f] infected with
Flag-T4 virus, BICv, or Flag-T4 virus/BICv challenge.

| Virus | DPI or DPC | Monoclonal Antibody | |
|---|---|---|---|
| | | Anti-Flag | WH303 |
| Flag-T4 | 3[a] | +\+[e] | neg[g]\neg |
| | 5 | ++++\+++ | neg\neg |
| | 7 | ++\ND[d] | neg\neg |
| BIC | 3[a] | neg\neg | ++++\++++ |
| | 5 | neg\neg | ++++\++++ |
| | 7 | neg\neg | +++++\+++++ |
| Flag-T4/BICv | 1[b] | +++\+ | neg\neg |
| | 3 | +++\++++ | neg\neg |
| | 5 | +++\ND | neg\ND |
| | 7 | +++\++ | neg\neg |

[a] DPI: days post-infection.
[b] DPc: days post-challenge with BICv.
[c] Animals were infected with Flag-T4 and 3 days later challenged with BICv.
[d] ND: not determined.
[e] Reactivity in fluorescence was quantified from (+) to (+++++)
[f] Two animals were processed per group per time point..
[g] neg: staining indistinguishable from background.

All publications and patents mentioned in this specification are herein incorporated by reference to the same extent as if each individual publication or patent was specifically and individually indicated to be incorporated by reference.

The forgoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant classical swine virus (CSFV) mutant comprising a DNA sequence encoding a mutation in the E1 glycoprotein of said CSFV mutant, wherein the mutation comprises a 20 mer insertion (SEQ ID NO: 9) at nucleotide position 2429, wherein said 20 mer insertion comprises the FLAG™ epitope in the E1 glycoprotein of the CSFV mutant, said epitope consisting of the amino acid sequence, DYDDDDK (SEQ ID NO: 5) as the last eight amino acids of the insertion, wherein said recombinant CSFV mutant is a live attenuated CSFV and said FLAG™ epitope carried by said CSVF mutant is capable of being recognized by monoclonal antibodies specifically binding to said FLAG™ epitope, which serve as a positive mutation marker for said live attenuated CSFV mutant.

2. The recombinant live attenuated CSFV mutant of claim 1 further comprising a mutation in CSFV E2 glycoprotein in addition to said positive mutation marker in CSFV E1 glycoprotein, wherein the mutation of CSFV E2 glycoprotein comprises a substitution mutation in the wild-type WH303 immunodominant epitope, TAVSPTTLR set forth in SEQ ID NO: 2, at amino acids positions 829-837 with the epitope, TSFNMDTLR set forth in SEQ ID NO:4 as a negative marker for the mutation, thus resulting in an elimination of the wild-type WH303 immunodominant epitope and wherein said recombinant CSFV mutant is a live attenuated CSFV having both the positive mutation marker as a result of the mutation in CSFV E1 glycoprotein of claim 1 and the negative marker of the mutation as a result of the mutation in the wild-type WH303 immunodominant epitope in CSFV E2 glycoprotein.

3. The recombinant CSFV mutant of claim 2 comprising DNA having the sequence identified by SEQ ID NO: 1.

4. The recombinant CSFV mutant according to claim 1 wherein the CSFV mutant comprises additional attenuating mutations.

5. A vaccine composition comprising the recombinant CSFV mutant according to any one of claims 1, 2, 3 and 4.

6. An isolated cell infected with the CSFV mutant of any one of claims 1, 2, 3 and 4.

7. A method for the protection of swine against CSF, comprising administering to swine a live attenuated CSF vaccine comprising a recombinant CSFV mutant according to claim 1 in an amount effective to protect said swine from clinical CSF.

8. A method of distinguishing animals infected with CSFV from animals vaccinated with a live attenuated CSF vaccine comprising a recombinant CSFV mutant according to claim 1, comprising: analyzing serum from an animal under evaluation to determine if said serum binds specifically to the FLAG™ epitope.

9. A method for the protection of swine against CSF, comprising administering to swine a live attenuated CSF vaccine comprising a recombinant CSFV mutant according to any one of claims 2 and 3 in an amount effective to protect said swine from clinical CSF.

10. A method of distinguishing animals infected with CSFV from animals vaccinated with a live attenuated CSF vaccine comprising a recombinant CSFV mutant according to any one of claims 1, 2 and 3, comprising analyzing serum from an animal under evaluation to determine if the positive marker, the FLAG™ epitope, is present and if the negative marker, the WH303 epitope immunodominant, is absent.

* * * * *